(12) United States Patent
Doolittle (10) Patent No.: US 9,087,402 B2
(45) Date of Patent: Jul. 21, 2015

(54) AUGMENTING IMAGES WITH HIGHER RESOLUTION DATA

(71) Applicant: Microsoft Corporation, Redmond, WA (US)

(72) Inventor: Don Doolittle, Woodinville, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 192 days.

(21) Appl. No.: 13/802,300

(22) Filed: Mar. 13, 2013

(65) Prior Publication Data

US 2014/0267396 A1 Sep. 18, 2014

(51) Int. Cl.
*G06T 19/00* (2011.01)
*G06T 7/00* (2006.01)
*G06T 11/60* (2006.01)

(52) U.S. Cl.
CPC ............. *G06T 19/006* (2013.01); *G06T 7/0024* (2013.01); *G06T 11/60* (2013.01)

(58) Field of Classification Search
None
See application file for complete search history.

(56) References Cited

U.S. PATENT DOCUMENTS

| 6,147,709 | A | 11/2000 | Martin et al. | |
|---|---|---|---|---|
| 6,580,427 | B1* | 6/2003 | Orenstein et al. | 345/422 |
| 7,965,314 | B1 | 6/2011 | Miller et al. | |
| 8,634,848 | B1* | 1/2014 | Bozarth et al. | 455/456.1 |
| 2002/0057279 | A1 | 5/2002 | Jouppi | |
| 2003/0234866 | A1* | 12/2003 | Cutler | 348/207.1 |
| 2004/0003409 | A1 | 1/2004 | Berstis | |
| 2005/0129324 | A1* | 6/2005 | Lemke | 382/254 |
| 2008/0088698 | A1* | 4/2008 | Patel et al. | 348/14.09 |
| 2008/0143842 | A1* | 6/2008 | Gillard et al. | 348/218.1 |
| 2008/0174670 | A1* | 7/2008 | Olsen et al. | 348/222.1 |
| 2008/0278474 | A1* | 11/2008 | Benman | 345/418 |
| 2009/0067707 | A1 | 3/2009 | Sim et al. | |
| 2009/0110291 | A1* | 4/2009 | Matsumura et al. | 382/195 |
| 2009/0175492 | A1* | 7/2009 | Chen et al. | 382/100 |
| 2009/0324062 | A1 | 12/2009 | Lim et al. | |
| 2010/0001880 | A1* | 1/2010 | Kraft et al. | 340/905 |
| 2010/0046846 | A1 | 2/2010 | Brown | |
| 2010/0331043 | A1* | 12/2010 | Chapman et al. | 455/556.1 |
| 2011/0115886 | A1* | 5/2011 | Nguyen et al. | 348/47 |
| 2011/0181621 | A1* | 7/2011 | Ohba et al. | 345/629 |
| 2011/0279445 | A1* | 11/2011 | Murphy et al. | 345/419 |
| 2011/0304699 | A1* | 12/2011 | Ito et al. | 348/47 |
| 2013/0067524 | A1* | 3/2013 | Andrews et al. | 725/109 |

(Continued)

OTHER PUBLICATIONS

Xiong, et al., "Robust Web Image/Video Super-Resolution", Retrieved at <<http://research.microsoft.com/en-us/people/fengwu/superresolution_tip_10.pdf>>, In IEEE Transactions on Image Processing, vol. 19, Issue 8, Aug. 2010, pp. 12.

(Continued)

*Primary Examiner* — David H Chu
(74) *Attorney, Agent, or Firm* — Judy Yee; Micky Minhas (57) ABSTRACT

Embodiments are disclosed that relate to augmenting a lower resolution image with higher resolution image data. For example, one disclosed embodiment provides a method comprising imaging a scene with a first, lower resolution imaging device to form a first set of image data. The scene may also be imaged with a second, higher resolution imaging device to form a second set of image data. The method further comprises augmenting at least a portion of the first set of image data with at least a portion of the second set of image data to form an augmented image.

19 Claims, 8 Drawing Sheets

(56) References Cited

U.S. PATENT DOCUMENTS

2014/0210950 A1* 7/2014 Atanassov et al. .............. 348/47
2014/0211989 A1* 7/2014 Ding et al. .................... 382/103

OTHER PUBLICATIONS

Skjervold, et al., "Bandwidth Optimizations for Standards-based Publish/Subscribe in Disadvantaged Grids", Retrieved at <<http:ieeexplore.ieee.org/stamp/stamp.jsp?tp=&arnumber=6415635>>, In Military Communications Conference, Oct. 29, 2012, pp. 8.

Rushdi, et al., "Augmented Coupled Dictionary Learning for Image Super-Resolution", Retrieved at <<http://ieeexplore.ieee.org/stamp/stamp.jsp?tp=&arnumber=6406579>>, In 11th International Conference on Machine Learning and Applications, vol. 1, Dec. 12, 2012, pp. 6.

Valiveti, et al., "Morphology Based Domain Partitioning of Multiphase Materials: A Preprocessor for Multi-scale Modelling", Retrieved at <<http://cmrl.jhu.edu/papers/2007-ijnme.pdf>>, In International Journal for Numerical Methods in Engineering, Jul. 31, 2006, pp. 38.

ISA European Patent Office, International Search Report & Written Opinion for PCT/US2014/023228, WIPO, Sep. 5, 2014, 15 Pages.

Elder et al., "Attentive Wide-Field Sensing for Visual Telepresence and Surveillance", In Neurobiology of Attention, May 26, 2004, 13 Pages.

* cited by examiner

AUGMENTING IMAGES WITH HIGHER RESOLUTION DATA

BACKGROUND

Imaging devices may be used to provide a live video stream of a scene for various applications. Often, the imaging devices and/or the video stream provide a low resolution representation of the scene in order to reduce device cost and/or reduce bandwidth utilized in transmitting the video stream. As such, the resolution of the video image during playback by a recipient device may be limited.

SUMMARY

Embodiments are disclosed herein that relate to augmenting a lower resolution image with higher resolution image data. For example, one embodiment provides a method comprises imaging a scene with a first, lower resolution imaging device to form a first set of image data, and also imaging the scene may be imaged with a second, higher resolution imaging device to form a second set of image data. The first set of image data may then be augmented with the second set of image data to form an augmented image having a higher quality than images from the first imaging device alone.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

Imaging devices may be utilized to provide a real-time representation of a scene for various applications, including but not limited to video communication systems and gaming applications. As mentioned above, some such imaging devices, such as web cams and/or image sensors for video game input, may be configured to capture lower resolution images in order to reduce bandwidth usage and/or device cost in comparison to systems that utilize relatively higher resolution images. However, low resolution imaging may result in the presentation of a lower quality video image by a device that receives and utilizes the image data.

Many common electronic devices, such as various smart phones, notepad computers, laptop computers, etc. include high resolution image sensors. As these devices are often carried continuously by users, these devices may be utilized to acquire higher quality images of a scene being imaged by a lower resolution video image sensor. Accordingly, embodiments are disclosed herein that relate to augmenting lower resolution images with higher resolution image data from a higher resolution image sensor. For example, in some embodiments, an appearance of relatively static features in a lower resolution video image, such as background scenery, may be augmented with higher resolution image data to increase a resolution of such features when the image is presented. As such features are static, they may be efficiently compressed so that bandwidth usage is not increased significantly. This may allow the higher resolution image data to be acquired a single time, or at a lower frame rate, than the lower resolution data, as higher resolution image data of static features in a scene from one frame may be used to augment multiple frames of lower resolution image data. Further, in some embodiments, the higher resolution image data may be transmitted to a receiving device (e.g. as a single frame or at a lower frame rate) separately from the lower resolution image data, and augmentation may be performed on the receiving device. It will be understood that these examples are intended to be illustrative and not limiting.

Figure 1:
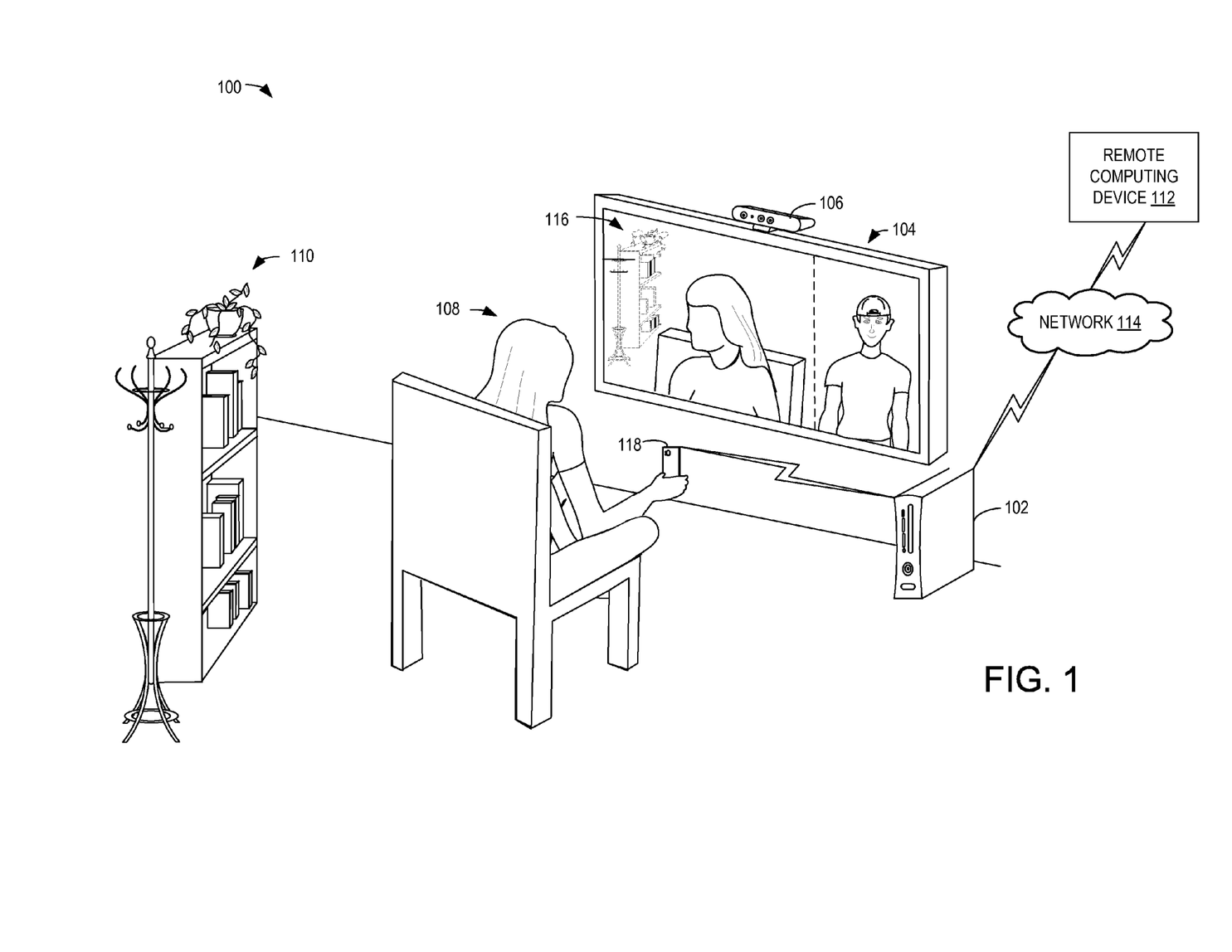
FIG. 1 shows a user interacting with a video chat program via a low resolution camera.

FIG. 1 shows a non-limiting example of a video communication environment 100. Video communication environment 100 comprises a computing device 102 that may be used to play a variety of different games, play one or more different media types, and/or control or manipulate non-game applications and/or operating systems. FIG. 1 also shows a display device 104, such as a television or a computer monitor, which may be used to present media content, game visuals, etc., to users. A first imaging device 106 is also shown in environment 100, which may be used to image a scene including a user 108 and one or more objects 110. While illustrated as a room in FIG. 1, it will be appreciated that environment 100 may comprise any suitable physical location, number of people, and number and/or type of objects. For example, objects may include non-person entities, including but not limited to inanimate objects, animals, plants, etc.

The first imaging device 106 may be operatively connected to the computing device 102 via one or more interfaces. As a non-limiting example, the computing device 102 may include a universal serial bus (USB) to which the first imaging device 106 may be connected. The first imaging device 106 may capture one or more images to form a live video feed of the scene and send corresponding image data to a computing device 102 via the one or more interfaces. In order to capture information about the scene, the first imaging device 106 may include any suitable sensors. For example, the first imaging device 106 may include a two-dimensional camera (e.g., an RGB camera), a depth camera system (e.g., a time-of-flight and/or structured light depth camera), a stereo camera arrangement, one or more microphones (e.g., a directional microphone array), and/or any other suitable sensors.

The computing device 102 may display received images on the display device 104 and/or send the images to a remote computing device 112 via a network 114 in order to provide a video communication session. In some embodiments, the first imaging device 106 may be configured to capture image data at a relatively lower resolution, e.g. at 640×480 pixels. However, at such resolutions, some objects may appear less sharp and/or otherwise have a lower quality appearance than with a higher resolution image sensor. For example, as depicted in the display device 104, the low resolution representation 116 of object 110 is unclear, and detailed features of the object 110 may not be discernible. As a more specific example, hooks of the coat stand are not visible in the displayed image and the displayed image does not clearly show separations between books on the bookshelf. It will be understood that these particular features are described for the purpose of example, and that a low resolution image may manifest in various ways. For example, lower resolution images may provide fewer details pertaining to shape, color, texture, pattern, size, and/or any other suitable feature of a portion of a scene than relatively higher resolution images.

FIG. 1 also shows a non-limiting example of a second imaging device 118. The second imaging device 118 may comprise any suitable imaging device with a higher resolution image sensor than the first imaging device 106. For example, the second imaging device may take the form of a digital camera, a smart phone comprising a high resolution camera, a tablet computer comprising a high resolution camera, and/or any other suitable type of device. The second imaging device 118 may be configured to communicate with one or more additional computing devices, such as the computing device 102, via any suitable wired and/or wireless communication technique.

The second imaging device 118 may acquire image data capturing the scene, and transmit the image data to the computing device 102. The computing device 102 then may process this image data and the image data from the first imaging device 106 to form augmented images comprising a combination of lower resolution image data and higher resolution image data. This may help to sharpen the appearance of the images displayed by a presenting device (e.g. a recipient device in a video communication session) relative to unaugmented images from the first imaging device 106.

Figure 2:
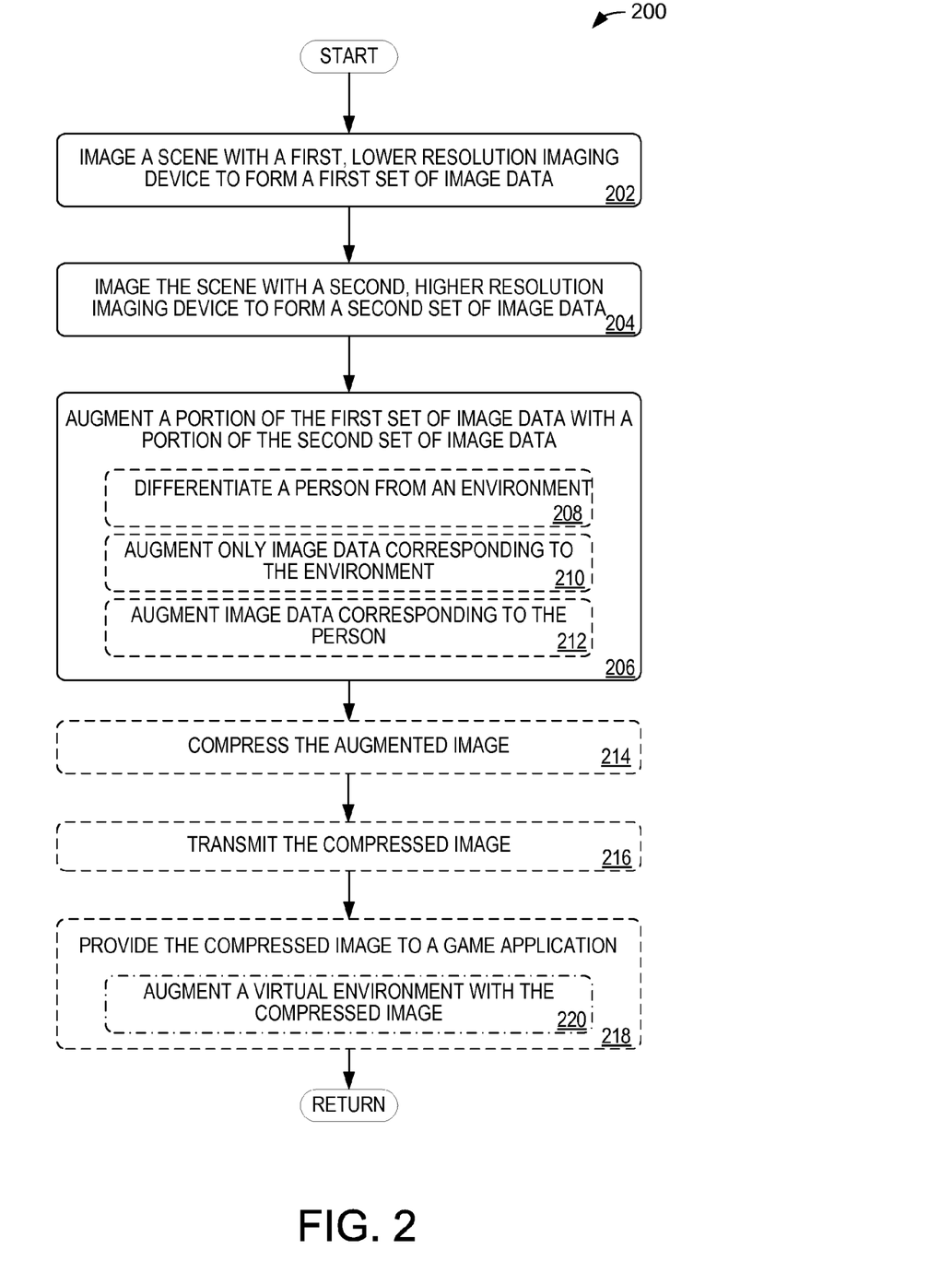
FIG. 2 shows a flow diagram depicting an embodiment of a method of augmenting lower resolution image data with higher resolution image data.

FIG. 2 shows a method 200 of augmenting an image in accordance with an embodiment of the present disclosure. Method 200 may be performed by any suitable computing device, including but not limited to computing device 102 of FIG. 1. Examples of other suitable computing devices include, but are not limited to, mobile devices, notepad computers, laptop computers, desktop computers, etc. At 202, method 200 includes imaging a scene with a first, lower resolution imaging device to form a first set of image data. For example, the first, lower resolution image device may correspond to imaging device 106 of FIG. 1 in some embodiments. At 204, method 200 includes imaging the scene with a second, higher resolution imaging device to form a second set of image data. For example, the second, higher resolution imaging device may comprise a rear-facing camera on the second imaging device 118. It will be understood that the second image data may be acquired and provided to the computing device 102 at the request of the user 108, at the request of the computing device 102, or upon the occurrence of any other suitable trigger. It will be appreciated that the second imaging device may image the scene at any suitable time relative to the first imaging device.

Figure 3:
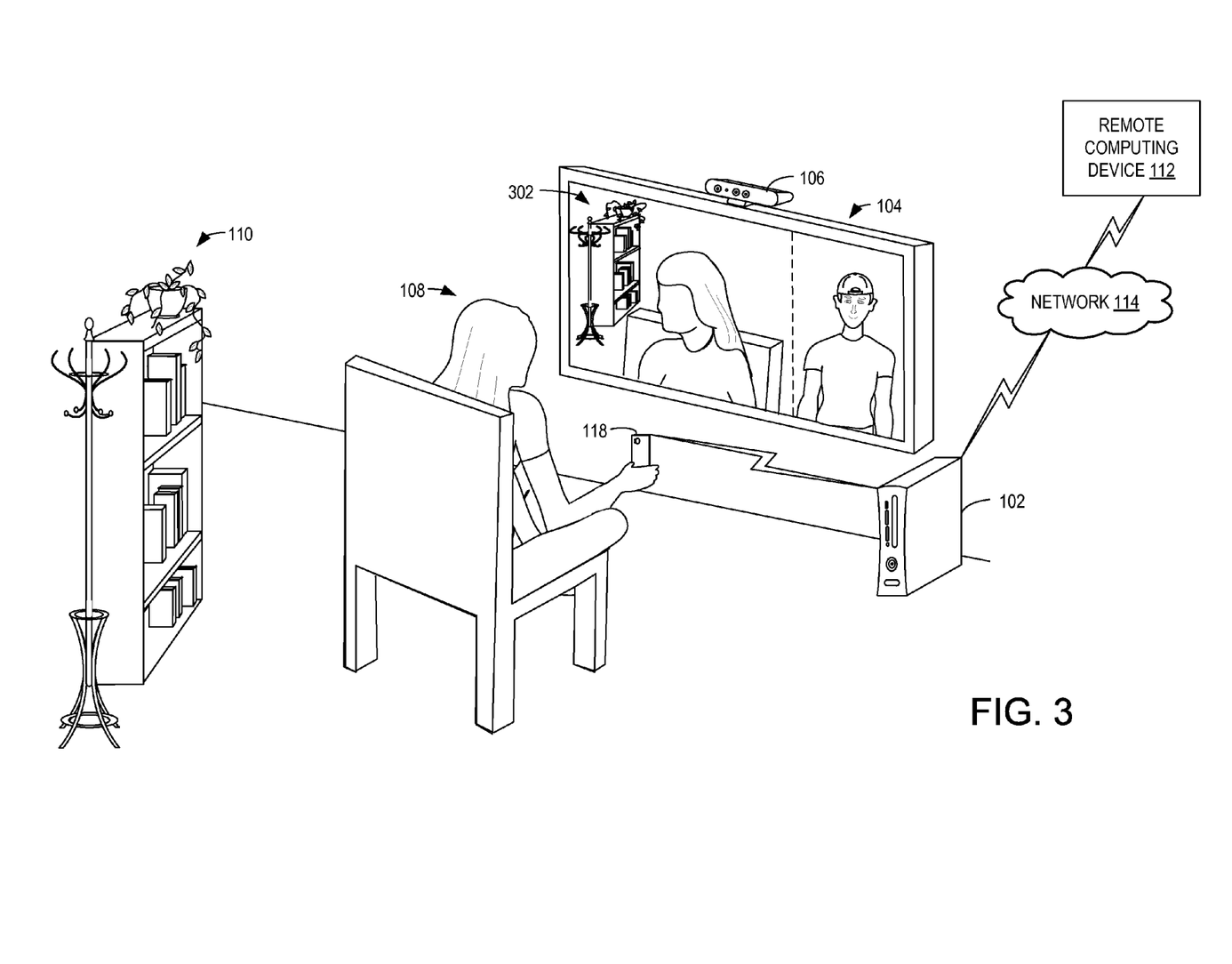
FIG. 3 shows a user interacting with a video chat program in which low resolution image data is augmented with higher resolution image data according to an embodiment of the present disclosure.

Method 200 further includes augmenting a portion of the first set of image data with a portion of the second set of image data, as indicated at 206. In some embodiments, the augmenting process may include, for example, differentiating a person from an environment, as indicated at 208, and augmenting image data corresponding to the environment, as indicated at 210, to the exclusion of image data corresponding to the person. Turning briefly to FIG. 3, the environment of FIG. 1 is shown with an augmented image being displayed via display device 104. As depicted, the augmented representations 302 of objects 110 are much clearer and provide additional detail in comparison to the low resolution representations 116 of objects 110 of FIG. 1. For example, the hooks of the coat stand are more clearly visible and the separations between the books are distinguishable. In the example of FIG. 3, image data corresponding to the background environment is augmented to the exclusion of image data corresponding to the user 108. In some scenarios, a portion of the background environment may be augmented, while in still other embodiments, an entire background environment may be augmented. As indicated at 212, the method 200 of FIG. 2 further may include augmenting image data corresponding to the person.

Continuing with FIG. 2, method 200 may include compressing the augmented image, as indicated at 214, to reduce an amount of data transmitted. As mentioned above, the resolution of video communication image sensors may be configured to be lower to preserve bandwidth and prevent visible lag in the presentation of video images. Where the higher resolution image data is used to augment image features such as background environment features, the higher resolution image data may change little from frame to frame. As such, the higher resolution image data may be efficiently compressed via a difference-based compression technique that encodes differences between image data frames. It will be understood that any additional or alternative compression techniques also may be used to compress augmented images.

Method 200 further may include, at 216, transmitting the compressed image to a receiving device. For example, in the video communication environment of FIG. 1, the compressed image may be transmitted to remote computing device 112 during a video communication session. In other embodiments, method 200 may include providing the compressed image to a game application, as indicated at 218. In such embodiments, the game application may augment a virtual environment with the compressed image at 220 in order to provide an immersive gaming experience that includes a user and/or a user environment.

Further, as mentioned above, in some embodiments, higher resolution image data may be transmitted separately from lower resolution image data. For example, higher resolution image data may be transmitted once (e.g., upon initialization of a video communication session) or at a lower frame rate than lower resolution image data, for augmentation at the receiving device. In such embodiments, either or both of the lower resolution and higher resolution data may be compressed for transmission.

Figure 4:
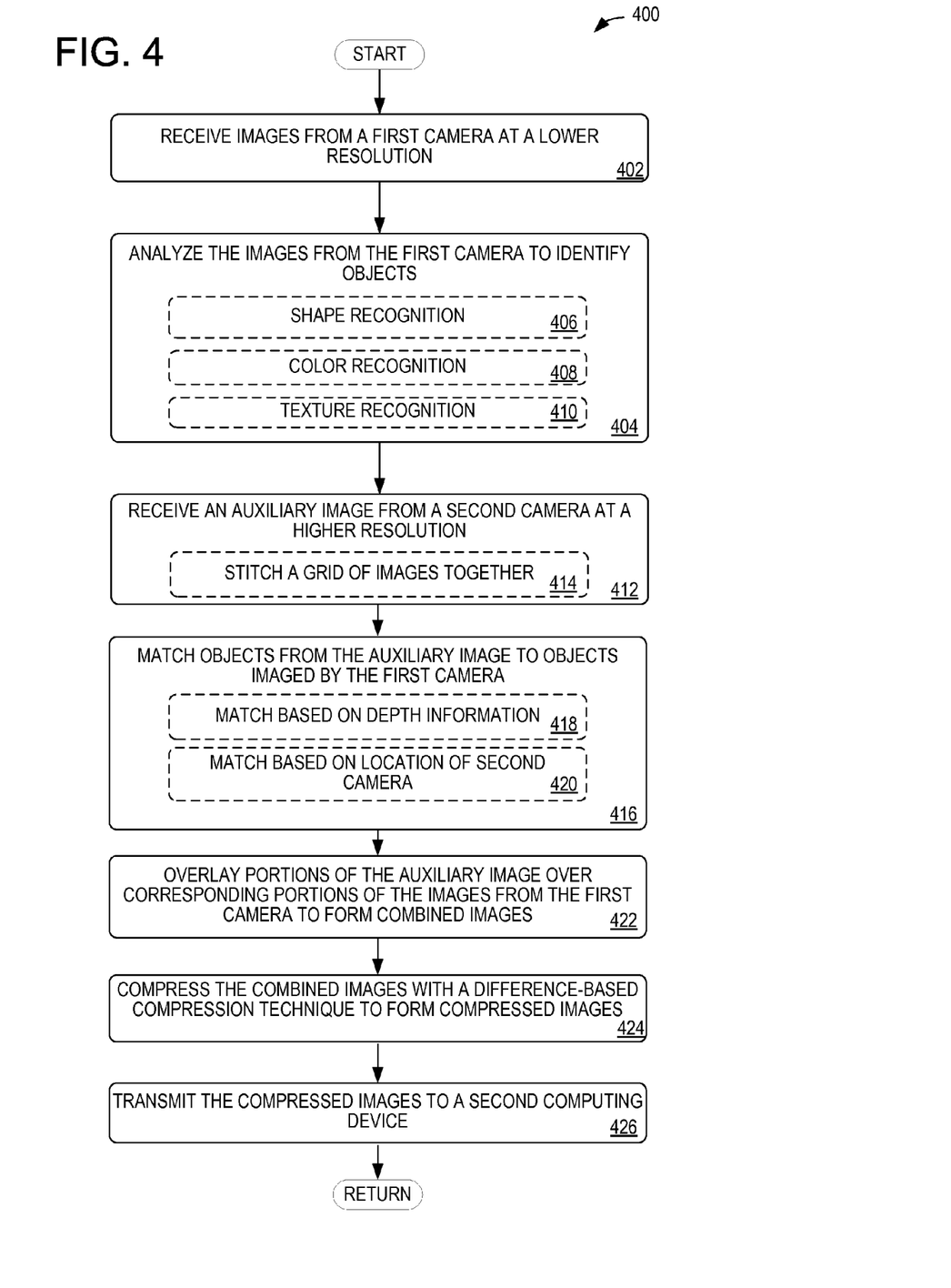
FIG. 4 shows a flow diagram depicting another embodiment of a method of augmenting lower resolution image data with higher resolution image data.

FIG. 4 shows a flow diagram depicting another embodiment of a method 400 for augmenting lower resolution images with higher resolution image data, in the context of augmenting image data in a video communication session. Method 400 includes receiving images from a first camera at a lower resolution relative to another imaging device, as indicated at 402. For example, the images of the first camera may correspond to a live video stream of a scene at the lower resolution. At 404, method 400 includes analyzing the images from the first camera to determine and/or identify one or more objects in the scene. For example, the one or more objects identified may be positioned in a background and/or a foreground of the scene. As a more specific example, in some embodiments, a person may be identified during the analysis via techniques such as facial recognition.

As indicated at 406, this analysis also may comprise performing shape recognition, e.g. using classification techniques or any other suitable shape recognition techniques. The computing device further may perform color recognition and/or texture recognition to help identify objects, as indicated at 408 and 410, respectively. For example, a region having the same or similar texture and/or color as an object in an image received from a second imaging device may be determined to correspond to a same object in each image. Likewise, such information also may be compared to object models to help identify objects. In some embodiments, image data from the first camera may include and/or be supplemented with depth information from a depth camera. Accordingly, one or more of the shape recognition, color recognition, and texture recognition may be performed using the depth information.

Figure 5:
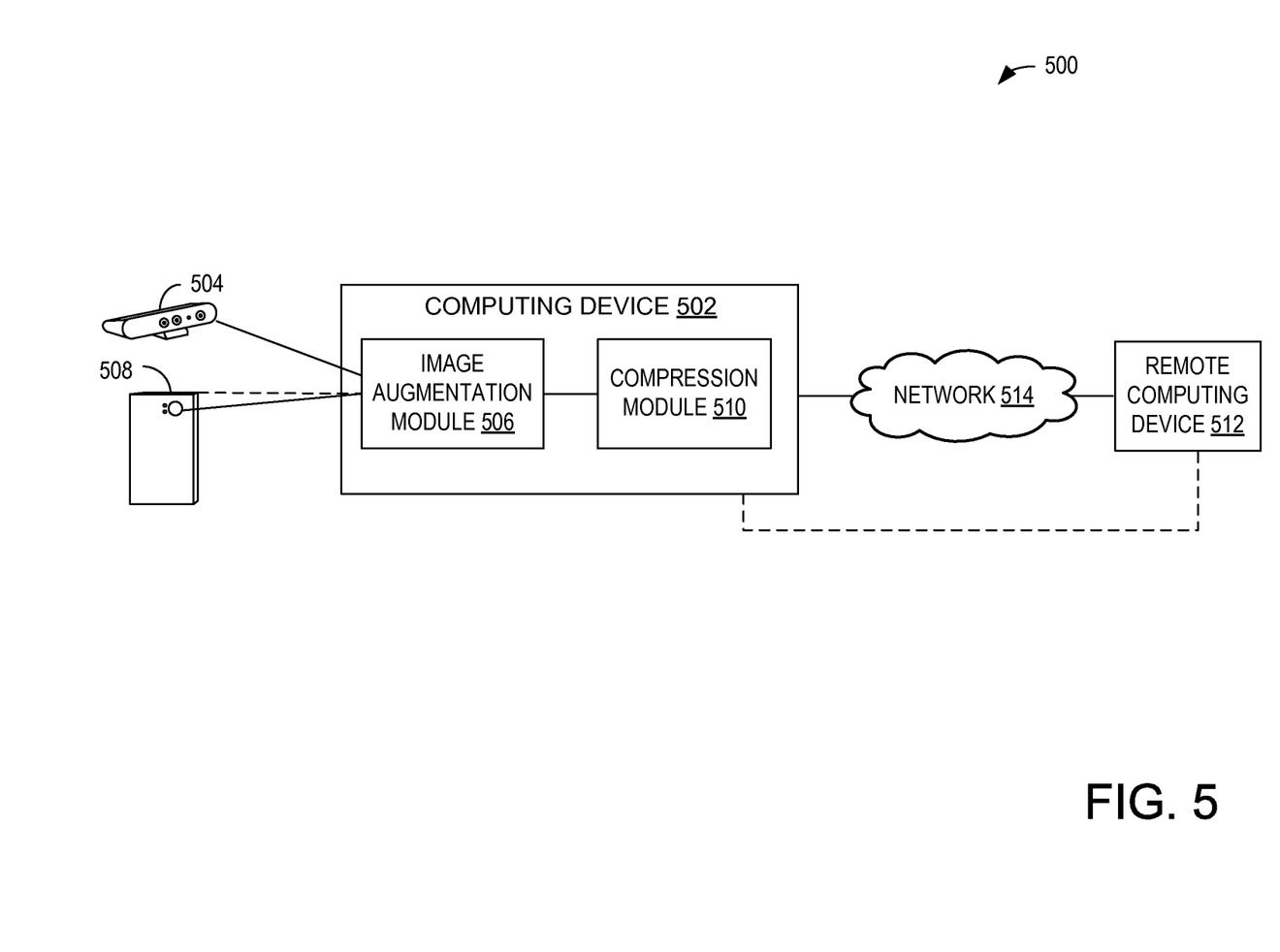
FIG. 5 shows a block diagram of a system for augmenting lower resolution image data with higher resolution image data and compressing the augmented image data for transmission to a remote computing device.

Turning briefly to FIG. 5, a high-level block diagram of an embodiment of a system 500 for augmenting an image is illustrated. The system 500 includes a computing device 502, which may comprise stored instructions that are executable to perform method 400 of FIG. 4. Images received from a first camera 504 may be processed via an image augmentation module 506 configured to perform, among other tasks, object identification analysis (or analyses), as described above.

Continuing with FIG. 4, method 400 further includes receiving an auxiliary image from a second camera at a higher resolution, as indicated at 412. Referring again to FIG. 5, a second camera 508 is depicted as providing images to the image augmentation module 506. In some embodiments, the first camera and second camera may be integrated into a single computing device. For example, a computing device may comprise a smart phone including a front-facing camera and a rear-facing camera, wherein the front-facing camera may have a lower resolution than the rear-facing camera. In other embodiments, the first and second cameras may be located on different devices.

In some scenarios, the field of view of the second camera and/or the auxiliary image at least partially overlaps the field of view of the first camera and/or associated images. In such scenarios, the higher resolution of the auxiliary image may provide additional detail for the portion of the scene compared to the detail provided by the images from the first camera. In other scenarios, the field of view of the second camera and/or auxiliary image may include portions of the scene that are not imaged by the first camera. For example, the auxiliary image may include supplemental objects that are not included in the image from the first camera.

The field of view of the second camera and/or auxiliary image may have any suitable size relative to the view of the first camera. Where the field of view of the second camera is smaller than the field of view of the first camera, the second camera may provide a larger effective field of view by stitching still images together prior to augmenting the images from the first camera, as indicated at 414. The second camera may also capture a panning video of the scene to capture a wider view of the scene via a plurality of frames. The use of video image data may provide additional information regarding the scene. For example, the video may identify people and/or objects in the scene that move over time.

Figure 6:
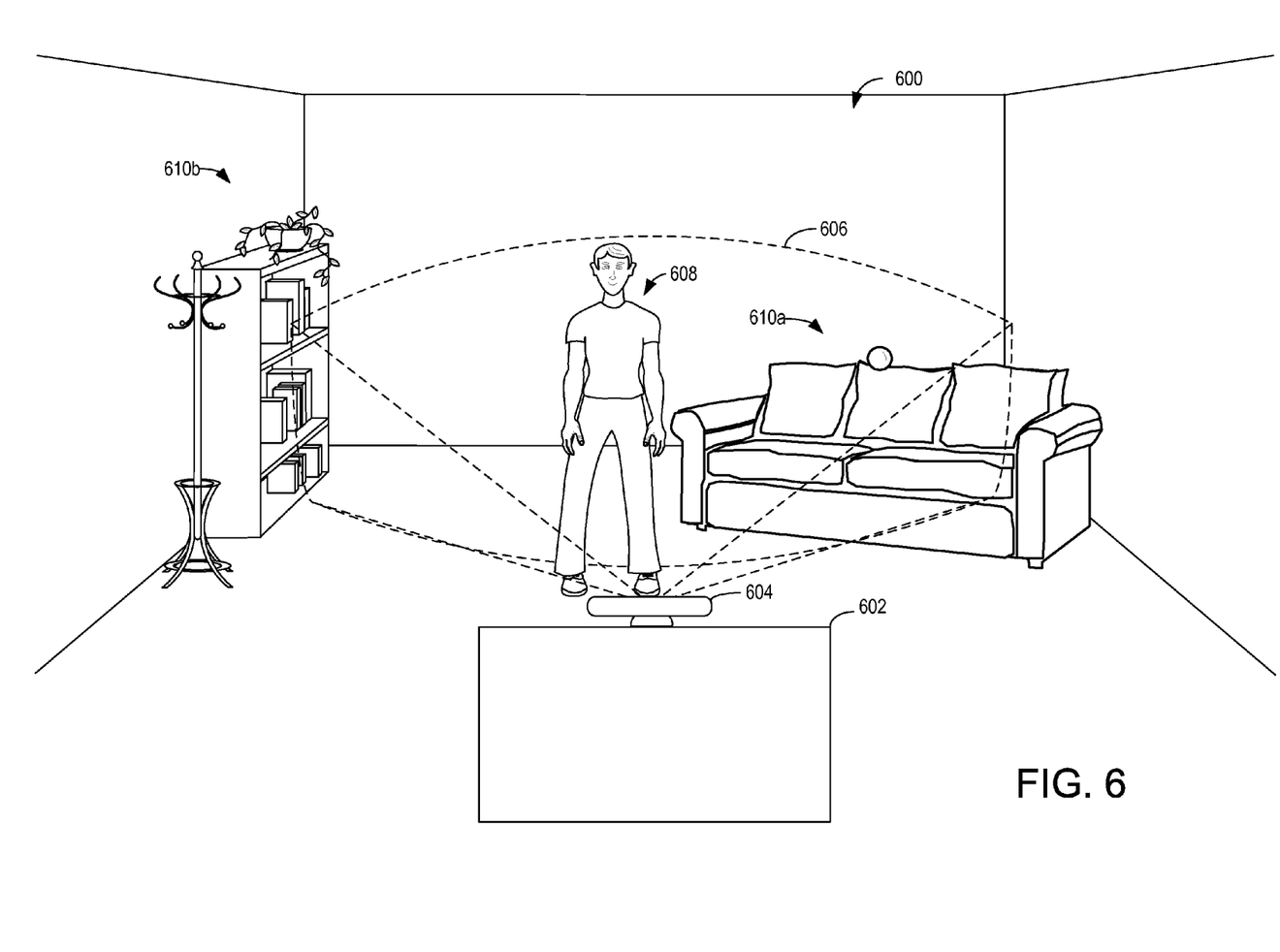
FIG. 6 shows a schematic illustration of a field of view of a lower resolution image sensor according to an embodiment of the present disclosure.
Figure 7:
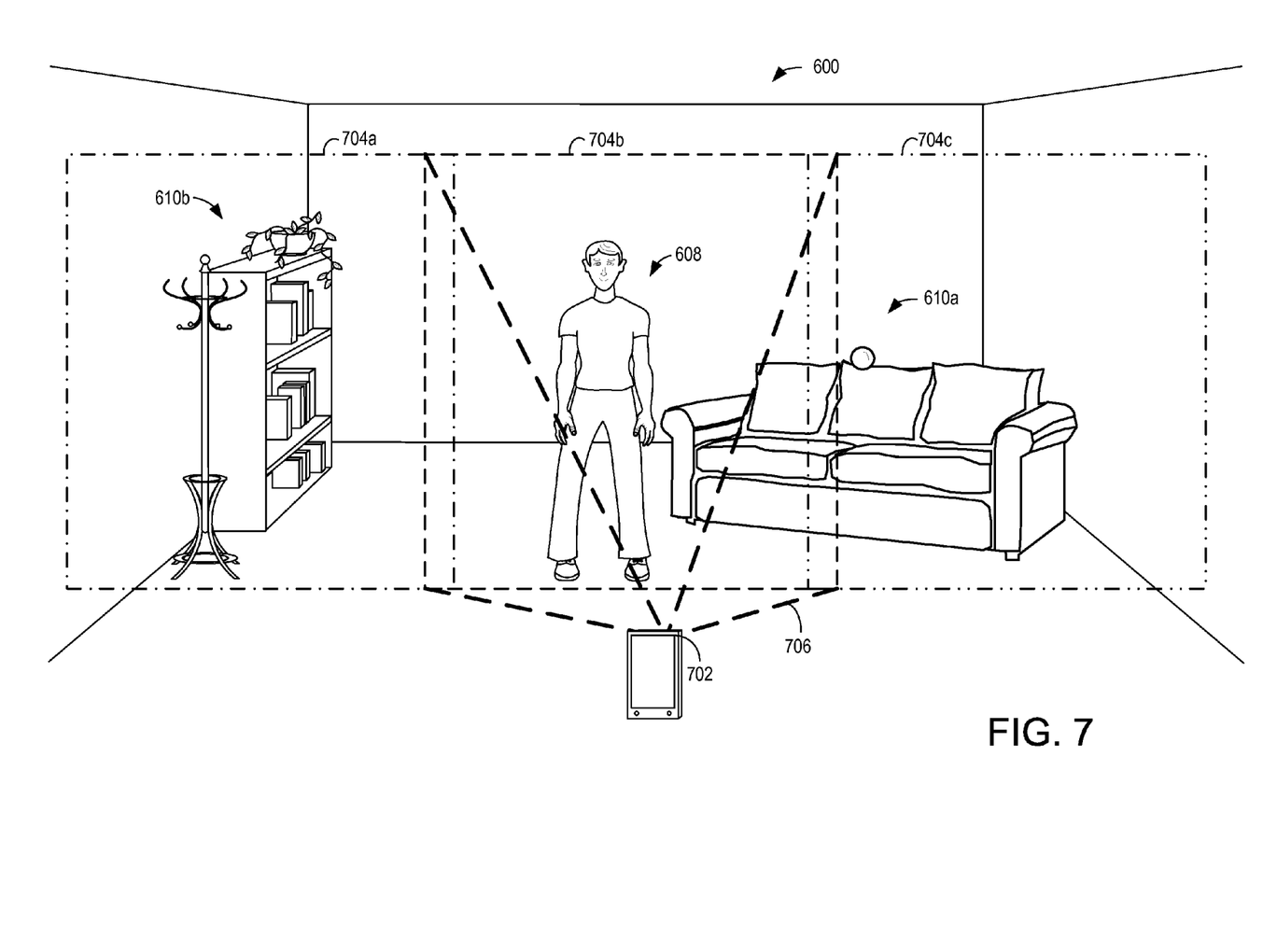
FIG. 7 shows a schematic illustration of a field of view of a higher resolution image sensor on a mobile device according to an embodiment of the present disclosure, and illustrates the stitching together of images acquired by the higher resolution image sensor.

Turning briefly to FIGS. 6 and 7, an example of stitching a plurality of images is illustrated. First, FIG. 6 depicts an environment 600 including a display device 602 and an imaging device 604. The dotted lines show a field of view 606 of the imaging device 604. As depicted, the field of view 606 includes a person 608 and a portion of objects 610a and 610b.

FIG. 7 illustrates an environment 600 including a mobile device 702 comprising a camera with a higher resolution than the imaging device 604 of FIG. 6. The depicted mobile device image sensor comprises a smaller field of view than the camera of imaging device 604. However, as depicted, the mobile device 702 may provide an effectively larger field of view by capturing a plurality of images, each of which images a different portion of the scene. As illustrated, the mobile device 702 captures a first image 704a, a second image 704b, and a third image 704c. The images then may be stitched together to form a single image having a field of view that is larger than that of the mobile device 702, represented by dashed line 706, as well as the field of view 606 of the imaging device 604 of FIG. 6, represented by dashed line. While some of the images of FIG. 7 are illustrated as overlapping horizontally, it is appreciated that the stitched images also may have any other suitable spatial relationship with one another.

Continuing with FIG. 4, method 400 includes matching objects from the auxiliary image to objects imaged by the first camera at 416 to spatially align the two images. The objects may be matched using any suitable comparison technique. For example, the computing device may perform edge analysis on the auxiliary image to match edges in the auxiliary image to corresponding edges in the images from the first camera. Further, in some embodiments, the objects may optionally be matched based on depth information of the objects and/or the scene received from a depth camera, as indicated at 418. For example, depth information associated with an object imaged by the first camera may be compared to one or more portions of the auxiliary image to identify the object in the auxiliary image. Additionally, classification methods may be used to identify objects, and the objects may be matched at least partially based upon identity.

In additional or alternative embodiments, the objects may optionally be matched based on a determined location and estimated field of view of the second camera, as indicated at 420. For example, the computing device may determine a location and/or orientation of the second camera from information in image data from the first camera, or may receive such information from the mobile device as determined based upon global positioning system, compass, and/or inertial motion sensor data from sensors on the mobile device. The location and/or orientation information, in combination with an estimated field of view of the second camera, may be utilized to determine a position of the portion of the scene imaged by the second camera relative to the position of the portion of the scene imaged by the first camera. Based on the relative position of the two portions of the scene, objects that are common to both portions may be matched.

At 422, the method 400 includes overlaying portions of the auxiliary image over corresponding portions of the images from the first camera to form augmented images. In some embodiments, the entire auxiliary image may be overlaid over an image from the first camera, while in other embodiments a portion of the second image may be used to augment a portion of the first image.

As overlaying higher resolution image data over lower resolution image data may increase a size of the combined image relative to the lower resolution image, in order to preserve bandwidth when transmitting augmented image data, method 400 includes compressing the combined image to form compressed images, as indicated at 424. In some embodiments, a difference-based compression method may be used, while in other embodiments any other method or methods may be used. Referring briefly to FIG. 5, a compression module 510 is shown for applying one or more compression techniques to augmented and/or combined images received from the image augmentation module 506.

Referring again to FIG. 4, as indicated at 426, method 400 includes transmitting the compressed images to a second computing device, for example, in a video communication session. This is shown in FIG. 5 as compressed images from the compression module 510 being transmitted to the remote computing device 512 via a network 514. The computing device 502 may communicate with the remote computing device 512 via any suitable wired or wireless communication protocol, and via any suitable network or networks, including but not limited to computer networks and telephone networks. Further, in some embodiments, the computing device 502 may connect to and transmit information to the remote computing device 512 directly without accessing the network 514.

Thus, low resolution images may be augmented with higher resolution image data to provide increased detail without unduly increasing bandwidth usage. In some embodiments, the methods and processes described herein may be tied to a computing system of one or more computing devices. In particular, such methods and processes may be implemented as a computer-application program or service, an application-programming interface (API), a library, and/or other computer-program product.

Figure 8:
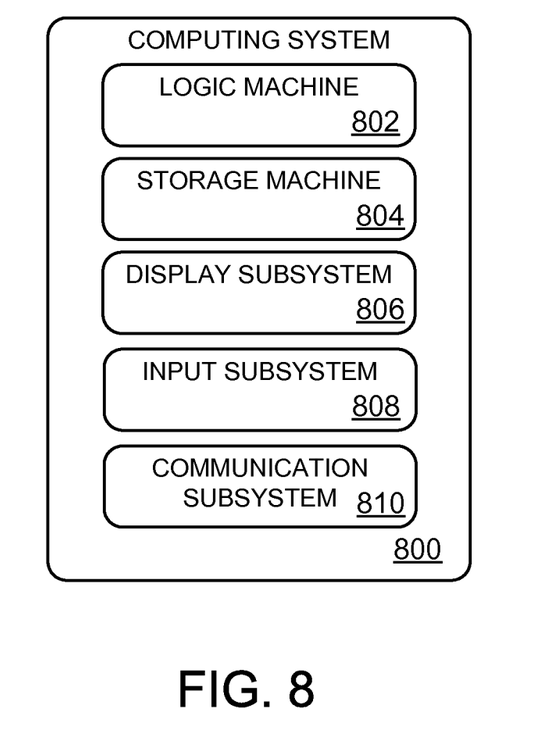
FIG. 8 shows an example embodiment of a computing device.

FIG. 8 schematically shows a non-limiting embodiment of a computing system 800 that can enact one or more of the methods and processes described above. Computing system 800 is shown in simplified form. Computing system 800 may take the form of one or more gaming consoles, personal computers, mobile communication devices (e.g., smart phone), mobile computing devices, tablet computers, home-entertainment computers, server computers, control devices, network computing devices, and/or other computing devices. For example, computing system 800 may include computing device 102 of FIG. 1.

Computing system 800 includes a logic machine 802 and a storage machine 804. Computing system 800 may optionally include a display subsystem 806, input subsystem 808, communication subsystem 810, and/or other components not shown in FIG. 8.

Logic machine 802 includes one or more physical devices configured to execute instructions. For example, the logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

The logic machine may include one or more processors configured to execute software instructions. Additionally or alternatively, the logic machine may include one or more hardware or firmware logic machines configured to execute hardware or firmware instructions. Processors of the logic machine may be single-core or multi-core, and the instructions executed thereon may be configured for sequential, parallel, and/or distributed processing. Individual components of the logic machine optionally may be distributed among two or more separate devices, which may be remotely located and/or configured for coordinated processing. Aspects of the logic machine may be virtualized and executed by remotely accessible, networked computing devices configured in a cloud-computing configuration.

The storage machine 804 includes one or more physical devices configured to store and hold instructions (e.g., computer- and/or machine-readable instructions) executable by the logic machine to implement the methods and processes described herein. For example, the logic machine 802 may be in operative communication with a sensor interface (e.g. an interface of the imaging devices 106 and 118 of FIG. 1), and the storage machine 804. When such methods and processes are implemented, the state of the storage machine 804 may be transformed—e.g., to hold different data.

Storage machine 804 may include removable and/or built-in devices. Storage machine 804 may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. Storage machine 804 may include machine-readable volatile, nonvolatile, dynamic, static, read/write, read-only, random-access, sequential-access, location-addressable, file-addressable, and/or content-addressable devices.

It will be appreciated that storage machine 804 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 802 and storage machine 804 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

When included, display subsystem 806 may be used to present a visual representation of data held by storage machine 804. This visual representation may take the form of a graphical user interface (GUI). As the herein described methods and processes change the data held by the storage machine, and thus transform the state of the storage machine, the state of display subsystem 806 may likewise be transformed to visually represent changes in the underlying data. Display subsystem 806 may include one or more display devices utilizing virtually any type of technology. Such display devices may be combined with logic machine 802 and/or storage machine 804 in a shared enclosure, or such display devices may be peripheral display devices. For example, display subsystem 806 may include display device 104 of FIG. 1.

When included, input subsystem 808 may comprise or interface with one or more user-input devices such as a keyboard, mouse, touch screen, microphone, or game controller. For example, input subsystem may include or interface with computing device 102 and/or second imaging device 118 of FIG. 1. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity.

When included, communication subsystem 810 may be configured to communicatively couple computing system 800 with one or more other computing devices. Communication subsystem 810 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 800 to send and/or receive messages to and/or from other devices via a network such as the Internet.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. On a computing device, a method of augmenting a lower resolution image with higher resolution image data, the method comprising:
    imaging a scene with a first, lower resolution imaging device to form a first set of image data;
    imaging the scene with a second, higher resolution imaging device to form a second set of image data;
    identifying a relative location of the second imaging device; and
    augmenting at least a portion of the first set of image data with at least a portion of the second set of image data by determining a position of an object in the second set of image data based on the relative location of the second imaging device, matching the position of the object in the second set of image data with a position of a corresponding object in the first set of image data, and overlaying at least a portion of the second set of image data over at least a portion of the first set of image data to form an augmented image.

2. The method of claim 1, further comprising compressing the augmented image with a difference-based compression technique to form a compressed image.

3. The method of claim 2, wherein the computing device comprises a first computing device, the method further comprising transmitting the compressed image to a second computing device during a video communication session between the first computing device and the second computing device.

4. The method of claim 2, further comprising providing the compressed image to a game application of the computing device, the game application augmenting a virtual environment with the compressed image.

5. The method of claim 1, further comprising receiving multiple images from the second imaging device and stitching the multiple images together to form a stitched image prior to augmenting the first set of image data.

6. The method of claim 1, wherein the first set of image data includes a first image captured by the first imaging device and the second set of image data includes a second image captured by the second imaging device, and wherein augmenting the first set of image data with the second set of image data includes overlaying at least a portion of the second image over the first image.

7. The method of claim 6, wherein overlaying the second image over the first image comprises performing an edge analysis to match objects of the scene present in both the first image and the second image.

8. The method of claim 1, wherein augmenting the first set of image data with the second set of image data includes differentiating a person in the scene from an environment of the scene and augmenting image data from the first set of image data corresponding to the environment.

9. The method of claim 1, wherein augmenting the first set of image data with the second set of image data includes differentiating a person in the scene from an environment of the scene and augmenting image data from the first set of image data corresponding to the person.

10. The method of claim 1, further comprising transmitting the first set of image data to a receiving device, transmitting the second set of image data to the receiving device, and wherein the augmenting is performed at the receiving device.

11. A system for imaging a scene, the system comprising:
    a computing device communicatively connected to a first camera and a second camera, the computing device comprising a logic machine and a storage machine configured to store instructions executable by the logic machine to
    receive a first, lower resolution image from the first camera;
    receive a second, higher resolution image from the second camera;
    identify a relative location of the second camera; and
    augment at least a portion of the first image with image data from the second image by determining a position of an object in the second image based on the relative location of the second imaging device, matching the position of the object in the second image with a position of a corresponding object in the first image, and overlaying at least a portion of the second image over at least a portion of the first image to form an augmented image.

12. The system of claim 11, wherein a field of view of the second camera at least partially overlaps with a field of view of the first camera.

13. The system of claim 11, wherein receiving the second image from the second camera further comprises receiving a plurality of images from the second camera, each of the plurality of images imaging a different portion of a scene.

14. The system of claim 11, wherein receiving the second image from the second camera further comprises receiving a plurality of frames of a video captured by the second camera, the plurality of frames capturing at least a portion of the scene over time.

15. The system of claim 11, wherein the first camera and the second camera are integrated into the computing device.

16. The system of claim 11, further comprising a depth camera, and wherein the instructions are executable to identify one or more objects in the first image based on depth information from the depth camera, and to match objects identified in the second image to the one or more objects from the first image identified by the depth information to spatially align the second image with the first image.

17. The method of claim 11, wherein the second camera has a larger field of view than the first camera.

18. On a first computing device, a method of augmenting image data in a video communication session between the first computing device and a second computing device, the method comprising:
    receiving images from a first camera to provide a live video stream of a scene at a first, lower resolution;

analyzing the images from the first camera to determine objects in a background of the scene and a foreground of the scene;

receiving an auxiliary image from a second camera at a second, higher resolution;

matching one or more objects from the auxiliary image to the objects in the background of the scene and the foreground of the scene to spatially align image data from the auxiliary image to image data received from the first camera;

overlaying one or more portions of the auxiliary image over one or more corresponding portions of the images received from the first camera to form one or more combined images;

compressing the one or more combined images utilizing a difference-based compression technique to form one or more compressed images; and transmitting the one or more compressed images to the second computing device.

19. The method of claim 18, wherein matching one or more objects from the auxiliary image to the objects in the background of the scene and the foreground of the scene further comprises matching a shape of the one or more objects from the auxiliary image to a shape of the objects in the background of the scene and the foreground of the scene.

* * * * *